United States Patent [19]

Schwartz et al.

[11] Patent Number: 5,380,663
[45] Date of Patent: Jan. 10, 1995

[54] AUTOMATED SYSTEM FOR PERFORMANCE ANALYSIS AND FLUORESCENCE QUANTITATION OF SAMPLES

[75] Inventors: Abraham Schwartz, Hato Rey, P.R.; Alan D. Hetzel, Starke, Fla.

[73] Assignee: Caribbean Microparticles Corporation, Hato Rey, P.R.

[21] Appl. No.: 110,632

[22] Filed: Aug. 23, 1993

Related U.S. Application Data

[63] Continuation of Ser. No. 671,198, Mar. 18, 1991, abandoned, which is a continuation-in-part of Ser. No. 620,530, Nov. 21, 1990, Pat. No. 5,089,416, and a continuation-in-part of Ser. No. 516,056, Apr. 27, 1990, Pat. No. 5,084,394, each is a continuation-in-part of Ser. No. 374,435, Jun. 30, 1989, Pat. No. 5,093,234, which is a continuation-in-part of Ser. No. 128,786, Dec. 4, 1987, Pat. No. 4,857,451, which is a continuation-in-part of Ser. No. 805,654, Dec. 11, 1985, Pat. No. 4,774,189, which is a continuation-in-part of Ser. No. 685,464, Dec. 24, 1984, Pat. No. 4,767,206.

[51] Int. Cl.$^6$ .................. G01N 21/64; G01N 33/546
[52] U.S. Cl. .................. 436/10; 436/8; 436/800; 436/808; 435/967; 435/975; 422/61; 422/82.08; 356/441; 364/555; 364/413.08
[58] Field of Search ............... 422/61, 82.08; 435/7.21, 967, 975; 436/8–18, 63, 800, 808; 356/213, 243, 318, 441; 364/551.01, 554, 555, 413.08, 413.1

[56] References Cited

U.S. PATENT DOCUMENTS

| | | | |
|---|---|---|---|
| 4,035,316 | 7/1977 | Yen | 260/2.5 B |
| 4,157,323 | 6/1979 | Yen | 260/29.7 M |
| 4,162,282 | 7/1979 | Fulwyler | 264/9 |
| 4,247,434 | 1/1981 | Vanderhoff | 260/29.6 RB |
| 4,254,096 | 3/1981 | Monthony | 424/8 |
| 4,438,239 | 3/1984 | Rembaum | 525/54.1 |
| 4,511,662 | 4/1985 | Baran | 436/513 |
| 4,552,633 | 11/1985 | Kumakura | 204/159.21 |
| 4,605,630 | 8/1986 | Kung | 436/511 |
| 4,609,689 | 9/1986 | Schwartz | 523/202 |
| 4,656,144 | 4/1987 | Hosaka | 436/534 |
| 4,665,020 | 5/1987 | Saunders | 435/7 |
| 4,694,035 | 9/1987 | Kasai | 524/458 |
| 4,698,262 | 10/1987 | Schwartz | 428/402 |
| 4,699,826 | 10/1987 | Schwartz | 428/402 |
| 4,699,828 | 10/1987 | Schwartz | 428/402 |
| 4,714,682 | 12/1987 | Schwartz | 436/10 |
| 4,751,188 | 6/1988 | Valet | 436/63 |
| 4,767,206 | 8/1988 | Schwartz | 356/73 |
| 4,774,189 | 9/1988 | Schwartz | 436/10 |
| 4,828,984 | 5/1989 | Schwartz | 435/7 |
| 4,857,451 | 8/1989 | Schwartz | 435/7 |
| 4,867,908 | 9/1989 | Recktenwald | 252/408.1 |
| 4,868,126 | 9/1989 | Schwartz | 436/10 |
| 4,918,004 | 4/1990 | Schwartz | 435/7 |
| 5,084,394 | 1/1992 | Vogt et al. | 436/8 |
| 5,093,234 | 3/1992 | Schwartz | 435/7.21 |

*Primary Examiner*—David A. Redding
*Attorney, Agent, or Firm*—Olive & Olive

[57] ABSTRACT

A system for rapid microbead calibration of a flow cytometer including a suspension of quantitative fluorescent microbead standards and analytical software. The software is used to take information on the microbead suspension from a flow cytometer and analyze data, smooth curves, calculate new parameters and notify of expiration of the system.

19 Claims, 10 Drawing Sheets

SUMMARY:

Mol. Equiv. Sol. Flchrome. = exp ( ( Channel + 451.8397 ) / 99.4634 )

Average Residual % = 0.8170 [Acceptable]

Correlation Coef. (R^2) = 0.9986270

Fluor Threshold    Channel 174, MESF 540.32

DETAILED STATISTICS:

| | Blank | Bead#1 | Bead#2 | Bead#3 | Bead#4 | Bead#5 |
|---|---|---|---|---|---|---|
| Bead Population | 26 | 356 | 519 | 638 | 753 | 822 |
| Left Channel Number | 355 | 518 | 637 | 752 | 821 | 900 |
| Right Channel Number | 122 | 3368 | 17340 | 57365 | 182297 | 364804 |
| Left Channel MESF | 3334 | 17167 | 56791 | 180474 | 361155 | 799166 |
| Right Channel MESF | 2819 | 1168 | 1335 | 986 | 996 | 1416 |
| Event Count | 31.19 | 12.92 | 14.77 | 10.91 | 11.02 | 15.67 |
| Percent of Events | 38.80 | 3.53 | 1.74 | 1.13 | 0.82 | 0.74 |
| Percent CV | 152.33 | 457.30 | 573.32 | 707.77 | 789.79 | 857.96 |
| Mean Channel | 156 | 458 | 574 | 708 | 790 | 858 |
| Median Channel | 177 | 461 | 575 | 705 | 788 | 858 |
| Mode Channel | 28 | 41 | 75 | 66 | 66 | 100 |
| Mode Peak Height | 435 | 9325 | 29939 | 115683 | 263885 | 523700 |
| Mean Channel MESF | 451 | 9391 | 30144 | 115956 | 264445 | 523901 |
| Median Channel MESF | 557 | 9678 | 30448 | 112511 | 259181 | 523901 |
| Mode Channel MESF | 897.90 | 31.30 | 17.75 | 8.14 | 6.36 | 7.99 |
| Average Deviation | 59.11 | 16.16 | 9.98 | 7.98 | 6.50 | 6.39 |
| Standard Deviation | 3493.95 | 261.15 | 99.61 | 63.65 | 42.22 | 40.79 |
| Variance | 1.47 | 1.96 | 1.84 | 2.42 | 1.78 | 1.95 |
| Skewness | -0.55 | 2.47 | 1.43 | 6.46 | 1.09 | 2.26 |
| Kurtosis | | | | | | |

FIG. 5

History File Data

| Rec | Acq-Date | AR% | Thresh | MESF-SL | MESF-YI | Peak | Channels | | | |
|---|---|---|---|---|---|---|---|---|---|---|
| 1 | 14-MAY-90 | 0.567 | 197 | 112.8 | -595.6 | 0 | 435 | 572 | 720 | 812 | 888 |
| 2 | 15-MAY-90 | 0.260 | 412 | 112.5 | -551.4 | 126 | 475 | 614 | 765 | 851 | 927 |
| 3 | 17-MAY-90 | 0.742 | 206 | 113.4 | -604.0 | 0 | 434 | 569 | 718 | 811 | 890 |
| 4 | 18-MAY-90 | 0.532 | 203 | 113.0 | -600.2 | 0 | 432 | 570 | 718 | 810 | 886 |
| 5 | 21-MAY-90 | 0.584 | 188 | 111.9 | -585.9 | 0 | 437 | 572 | 720 | 811 | 886 |
| 6 | 22-MAY-90 | 0.735 | 191 | 112.1 | -588.8 | 0 | 437 | 570 | 718 | 810 | 887 |
| 7 | 23-MAY-90 | 0.668 | 199 | 112.3 | -594.6 | 0 | 433 | 567 | 716 | 807 | 884 |
| 8 | 24-MAY-90 | 0.573 | 199 | 112.6 | -596.1 | 0 | 433 | 569 | 718 | 809 | 885 |
| 9 | 25-MAY-90 | 0.666 | 204 | 113.4 | -603.0 | 0 | 434 | 570 | 719 | 811 | 890 |
| 10 | 29-MAY-90 | 0.589 | 196 | 111.9 | -590.9 | 0 | 432 | 567 | 715 | 806 | 881 |
| 11 | 30-MAY-90 | 0.649 | 453 | 113.2 | -603.3 | 89 | 432 | 568 | 717 | 809 | 887 |
| 12 | 1-JUN-90 | 0.623 | 194 | 112.2 | -591.3 | 0 | 435 | 570 | 718 | 809 | 886 |
| 13 | 4-JUN-90 | 0.506 | 191 | 112.0 | -588.2 | 0 | 435 | 572 | 719 | 810 | 885 |
| 14 | 5-JUN-90 | 0.643 | 353 | 100.1 | -450.6 | 137 | 466 | 584 | 718 | 800 | 867 |
| 15 | 6-JUN-90 | 0.758 | 386 | 99.5 | -448.7 | 144 | 463 | 578 | 712 | 794 | 861 |
| 16 | 7-JUN-90 | 0.715 | 362 | 99.2 | -440.3 | 144 | 468 | 583 | 717 | 799 | 864 |
| 17 | 7-JUN-90 | 0.715 | 362 | 99.2 | -440.3 | 144 | 468 | 583 | 717 | 799 | 864 |
| 18 | 8-JUN-90 | 0.817 | 540 | 99.5 | -451.8 | 174 | 460 | 574 | 708 | 790 | 858 |

FIG. 6

AUTOMATED SYSTEM FOR PERFORMANCE ANALYSIS AND FLUORESCENCE QUANTITATION OF SAMPLES

CROSS-REFERENCE TO RELATED APPLICATIONS

This is a continuation of application Ser. No. 07/671,198 filed Mar. 18, 1991 now abandoned, which is a continuation-in-part of U.S. patent application Ser. No. 07/620,530 filed Nov. 21, 1990 U.S. Pat. No. 5,089,416 now abandoned, and U.S. application Ser. No. 07/516,056 filed Apr. 27, 1990 U.S. Pat. No. 5,084,394 now abandoned, each of which is a continuation-in-part of U.S. patent application Ser. No. 07/374,435 filed Jun. 30, 1989 U.S. Pat. No. 5,093,234, which is a continuation-in-part of U.S. patent application Ser. No. 07/128,786 filed Dec. 4, 1987 and issued as U.S. Pat. No. 4,857,451 on Aug. 15, 1989, which is a continuation-in-part of U.S. patent application Ser. No. 06/805,654 filed Dec. 11, 1985 and issued as U.S. Pat. No. 4,774,189 on Sep. 27, 1988, which is a continuation-in-part of U.S. patent application Ser. No. 06/685,464 filed Dec. 24, 1984 and issued as U.S. Pat. No. 4,767,206 on Aug. 30, 1988. The disclosure of each of the above copending patent applications and the issued patents is hereby incorporated herein.

BACKGROUND OF THE INVENTION

1. Field of the Invention

This invention relates to a rapid integrated system which includes a premixed suspension of a plurality of populations of quantitative fluorescent microbead standards, and analytical software correlated to the microbeads. The system allows analysis of flow cytometer performance with the premixed microbeads.

2. Description of the Related Art

Flow cytometers are used to analyze biological cells and particles present in a fluid sample by intersecting a thin stream of the fluid by an illumination source, usually a laser beam. The resulting forward and right angle scattered and fluorescent light is analyzed with the photomultiplier tubes (PMTs) of the flow cytometer. The fluorescent channels of a flow cytometer which are designated by FL1, FL2, FL3 and so forth, are each set with barrier filters to detect a selected specific dye while filtering out signals from dyes that fluoresce at other wavelengths.

Fluorescent microbeads have been used to calibrate fluorescence instruments such as flow cytometers or fluorescence microscopes so that "positive" cells that fluoresce at a particular wavelength may be distinguished from non-fluorescent cells by differences in fluorescence intensity measurements. Reagents and cell preparation techniques may cause complications in the measurement of fluorescence intensity.

As discussed in U.S. Pat. Nos. 4,714,682 and 4,868,126, for each population group of highly uniform microbeads, the number of molecules of equivalent soluble fluorochrome per (MESF) which is necessary to give rise to the same level of fluorescence intensity as the microbeads is determinable using the following steps: (1) the fluorescence intensity of a suspension of microbeads is determined with a fluorometer as compared to solutions of the free fluorescent dye to determine the number of equivalent soluble dye molecules per unit volume of the microbead suspension; (2) the number of microbeads per unit volume is determined; and (3) the number of equivalent soluble dye molecules per unit volume is divided by the number of microbeads per unit volume of the suspension to yield the equivalent soluble fluorescent dye molecules per microbead in the particular microbead sample. The Molecules of Equivalent Soluble Fluorescence (MESF) value indicates the equivalent number of free fluorochrome molecules in a solution that would have the same emission intensity as the microbead standard. These units are only valid when the excitation and emission spectra of the standards and unknown samples are the same. The MESF per microbead in various microbead samples may then be plotted as a function of fluorescent intensity to calibrate a flow cytometer or fluorescence microscope. The disclosure of this patent and all other patents and patent applications discussed herein is incorporated by reference.

Microbeads having antibodies bound thereto are disclosed in U.S. Pat. No. 4,918,004. A kit of said microbeads contains at least two populations of uniformly sized microbeads in which the number of fluorescently labeled antibodies binding to each microbead in these populations is the same within each population but different from population to population. The antibodies may be directly or indirectly bound to the microbeads, with the phrase "directly or indirectly binding" in reference to microbeads and associated fluorescently labeled antibodies being intended to be broadly construed to encompass covalent bonding of the fluorescently labeled antibody directly to the microbead, as well as microbead systems wherein a linking group e.g., an immunological agent such as a protein or hapten is covalently bonded to the microbead, and the fluorescently labeled antibody is in turn covalently bonded or otherwise bound to this linking group. Thus, for example, the latter indirect binding may be effected by covalently bonding to the microbead a primary nonfluorescent antibody with which a secondary fluorescently labeled antibody is covalently bondable, i.e., the secondary fluorescently labeled antibody being a conjugate of the primary nonfluorescent antibody.

Each of the populations of antibody-containing microbeads is run on a flow cytometer or fluorescence microscope to determine its fluorescence intensity. A calibration plot is constructed of the number of fluorescently labeled antibodies as a function of fluorescence intensity so that a sample's unknown number of fluorescent antibodies may be calculated from its fluorescence intensity.

Many problems arise in flow cytometry with respect to uneven instrument performance from day to day and variations in and losses in microbead fluorescence and in variations due to different reagents, preparations and samples. When the results of flow cytometer use are being used for day-to-day clinical comparisons of a patient or comparisons between samples run on different days, it is critical that variations in instrument performance be recognized so that the results are not erroneously interpreted. It is also important that the technique of standardizing the flow cytometer not cause errors in the observations. When microbeads have lost fluorescence, they no longer can be relied upon for standardization or calibration purposes.

When multiply-labeled samples are run on a flow cytometer and a suspension of multiple microbead populations having different labels is used as a standard, it is often difficult to identify which microbeads are labeled with which dye so that the standard can function effectively for use with the samples.

It is therefore an object of this invention to provide a system comprising fluorescently-labeled microbeads and matched software for flow cytometer use, which provides a comprehensive solution to the problem of obtaining reproducible fluorescence intensity measurements.

It is another object of the invention to provide a microbead-software system which can be used objectively to evaluate and plot instrument performance and operating conditions.

It is a further object of the invention to provide a microbead-software system in which the software automatically analyzes a list mode file of premixed microbeads and generates a linear regression plot and statistical data to assess instrument linearity.

It is a further object of the invention to provide a microbead-software system to determine fluorescence threshold sensitivity.

It is a further object of the invention to provide a microbead-software system that allows unequivocal standardization with multiple fluorescent dyes, in which multiple list mode files may be obtained and processed together.

It is a further object of the invention to provide a microbead-software system to allow creation of a file of daily instrument performance.

It is a further object to provide a system where the life of the microbeads and of the software are correlated with each other.

Further objects of this invention are the rapidity of simplicity, accuracy, objectiveness, and cost-effectiveness of use of the microbead-software system.

Other objects and advantages will be more fully apparent from the following disclosure and appended claims.

SUMMARY OF THE INVENTION

In its most basic configuration, the system of the invention comprises a suspension of populations of fluorescent quantitative microbeads, and a first software program which is specifically formulated for each batch of microbeads so that the fluorescence values of each batch of microbeads and the date when the microbeads no longer should be used are included in the program. In addition to the two main components or instead of first software program, the system may include another software program which provides the capability of evaluating two or more flow cytometer channels for two or more fluorescent dyes. A third program may be provided which allows sequential gating, analysis, and subsequent re-gating and re-analysis of data obtained from a cell sample. Two further components, a suspension of microbeads having bound thereto fluorescently labeled antibodies and a software program specifically formulated for said antibody-containing microbeads may be included.

The integrated software-fluorescent microbeads standards system is a powerful tool for monitoring and optimizing fluorescence intensity measurements. An entire calibration and analysis can be completed in less than five minutes, and a daily report generated on a printer. All results are automatically recorded in a cumulative file history to provide comprehensive documentation of an instrument's performance.

Each microbead suspension comprises a plurality of populations of highly uniform microspheres. Fluorescein molecules are covalently bound on the outer surface of the labeled microbeads to insure consistency with measurements made on analytes or under a variety of conditions.

The software is matched to specific lots of microbead standards, since all fluorescent molecules are subject to degradation. Thus, for each batch of microbeads or antibody containing microbeads, the associated software program includes information on the fluorescence intensity of each population of microbeads within the batch. When the kit approaches its expiration date, the software alerts the operator. This assures that where standardization is monitored and critical, those monitoring printouts will know whether the microbeads are within the required range of fluorescence intensity. Daily calibration of flow cytometers using the microbeads and software of the invention allows objective comprehensive monitoring of fluorescence intensity without complications due to reagents, cell preparation techniques, operating conditions, or stained cell samples. Once the calibration is done, the actual amount of reagent bound by the stained sample cells may be determined. This measurement may be used to calculate the number of cell surface molecules (receptors) bound by particular reagents, which in turn, may be useful in characterizing cells that are activated, infected or neoplastic.

Additional calibrations may be indicated when instrument settings are changed or if it is important to document that samples within an entire run of samples are comparable and the measurements were stable.

In particular, the invention includes a kit for automated performance analysis and calibration for a flow cytometer analysis, comprising:

(a) a suspension of a plurality of populations of quantitative fluorescent microbeads and a nonfluorescently labeled microbead populations in a container, each of said fluorescent microbeads being bound to a first fluorescent dye, said fluorescent microbeads having a useful life, said useful life being designated in said kit; and (b) software containing information on the fluorescence intensity of each population of microbeads and being capable of indicating an expiration date correlated to the useful life of said microbeads.

The invention also comprises a method of calibrating and of determining performance of a flow cytometer, comprising:

(a) providing a premixed suspension of quantitative microbeads, said microbeads having a useful life, said microbeads suspension comprising a plurality of populations of microbeads, each of said populations having microbeads with a uniform size and a particular fluorescence intensity and differing from the other populations in fluorescence intensity, the microbeads of one of said populations having no added fluorescent dye and the remaining microbeads being bound to a first fluorescent dye;

(b) indicating that the microbeads have a useful life;

(c) providing software containing information on the fluorescence intensity of each population and being capable of indicating an expiration date correlated with the useful life of the microbeads;

(d) using said flow cytometer and said microbead suspension to provide an ungated list mode file of data for the microbead suspension on the flow cytometer; and (e) using said software to automatically gate and smooth the data, locate peaks in fluorescence intensity corresponding to each of the microbead populations, construct linear regression plots and determine the fluorescence threshold intensity of the flow cytometer.

The invention may be used for tissue typing using a flow cytometer by methods comprising:

(a) suspending cells of a potential donor in serum of a recipient;

(b) labeling said cells with an antibody;

(c) providing a suspension of microbeads, said microbeads having a uniform size and being calibrated to bind a known number of antibodies;

(d) saturating said microbeads with molecules of said antibody;

(e) providing software containing information on the antibody-binding capability of the microbeads;

(f) calibrating said flow cytometer;

(g) using said flow cytometer to determine list mode files from the cells and the microbeads;

(h) using the software of step (e) to calculate an effective fluorescence F/P ratio of the antibodies and the number of antibodies binding to the cells; and (i) comparing the number of antibodies binding to the cells to a standard for transplant tissue rejection to determine whether donor tissue should be given to the recipient.

Other aspects and features of the invention will be more fully apparent from the following disclosure and appended claims.

BRIEF DESCRIPTION OF THE DRAWINGS

FIG. 5 shows an example of a summary and detailed statistics of a report generated by using the first embodiment of the invention.

FIG. 6 shows history file data generated by using the first embodiment of the invention.

DETAILED DESCRIPTION OF THE INVENTION AND PREFERRED EMBODIMENTS THEREOF

Figure 1:
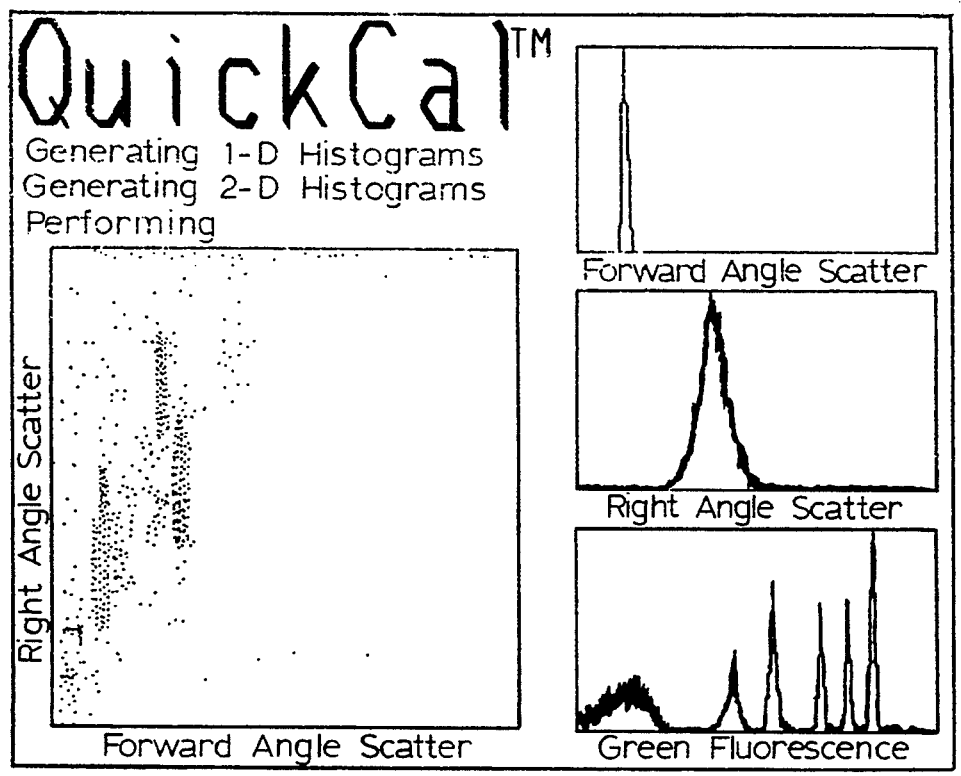
FIG. 1 is a representation of a screen display for the first embodiment of the software showing forward angle scatter, right angle scatter, green fluorescence and a plot of right angle scatter vs. forward angle scatter before smoothing.

The present invention comprises software that is tailored for use with a particular batch or suspension of quantitative fluorescent microbeads.

Preferably, each suspension of microbeads contains five populations of microbeads, with each population having a different amount of fluorescein label per microbead so that the fluorescence intensity differs between population, preferably from about 10,000 to about 500,000 MESF. Such a range spans the range of MESF values likely in most clinical samples. The preferred microbeads for use with the first embodiment of the software are designed to be used with cells labeled with fluorescein isothiocyanate (FITC). The spectra of the microbeads thus match the spectra of cells labeled with antibodies conjugated to FITC. Any other fluorescent label with which cells are labeled may be used. The microbeads may be prepared and labeled, for example, according to the methods of U.S. Pat. Nos. 4,767,206, 4,774,189 and 4,857,451. Microbeads being calibrated in numbering of antibodies may be bound thereto, when included within the kit of the invention as discussed below, are preferably prepared according to the method of U.S. Pat. No. 4,918,004. An unlabeled (blank) microbead population is included in each suspension to serve in obtaining the fluorescence threshold value as discussed below.

Preferably the microbead suspensions are provided in an opaque dropper bottle. The microbeads of the system of the invention are stable for the period shown on the bottle label when stored in their opaque bottle at 4° C. (without freezing). Fresh dilutions of the microbeads are run each time to obtain list mode files to avoid problems with degradation and photobleaching. Microbead suspensions should also be kept away from bright lights.

The populations of microbead standards are assigned calibration values by comparison with reference microbead standards analyzed on a flow cytometer. The reference microbead standards are traceable to direct photometric comparison with fluorescein solutions to provide the most accurate MESF values.

Each embodiment of the software as discussed below may be written for use on any computer, for example, Hewlett Packard computers, Elite workstations, and IBM computers. For example an IBM compatible 286 or 386 computer with a color (VGA) monitor may be used with an Epics Profile flow cytometer (Coulter Electronics Inc., Hialeah, Fla.), or an HP computer Model 9000 may be used which operates a FACScan or FACStar flow cytometer. The software is programmed to recognize list mode file data formats by reading its header. Preferably, with the FACScan or FACStar cytometer, FACScan Research Software, Lysys II (made by Becton Dickinson, San Jose, Calif.) or other software is used, which has full 1024 channel resolution retention of the data and also records the FACScan or FACStar instrument settings during acquisition of the data file so that it is easy to monitor operation of the flow cytometer.

The software of the invention preferably also contains the capability for allowing use of two or more instruments networked to the same disk storage or two or more specimen types or operators. The different list mode files are coded differently, for example, by placing a designating letter before the file designation, so that the program can sort and plot the file groups separately by prefix letter.

In the various embodiments of software discussed below, the preferred screen display design commands are discussed, but it should be clear that these may be varied in design or particular content or may be translated into other languages, etc, as preferred by users of the microbeads and software, without departing from the scope of the invention.

In a first embodiment (FIG. 8), the software program, termed QuickCal TM software, comprises a program which takes the information from an ungated list mode file of 10,000 events from premixed microbeads run on the flow cytometer and generates a histogram, and regression plot. A list mode calibration file is obtained with the microbeads used in the invention by standard flow cytometer operating techniques. In summary, the program automatically creates a dot plot and histograms, performs gating to remove all but the single peak on the forward and side scatter channels, recreates the histograms from the gated scatter data, smooths the data in the FL1 channel, locates the peak positions, constructs linear regression plots and derives the equation for the linear regression plots, calculates the coefficient of determination and average residual percent, determines the fluorescence threshold sensitivity of the instrument, and stores all the above information and the instrument setting in a history file for comparison with other information generated previously and afterward.

A more detailed description of the software follows. After allocating space and reading the designated list mode file, the first function performed by the Quick-Cal TM program is creation of the one ungated single parameter histogram (green fluorescence) and the ungated two dimensional histogram of the forward and right angle scatter. There should be six peaks in the green fluorescence (FIG. 1). The analysis is performed optimally when all the peaks are completely on scale. Just below the QuickCal TM title header on the viewer screen are three message lines of text which scroll upwards and indicate the function that is being performed or the actions to take by the user. These message lines preferably are monitored closely by the user of the software and microbeads.

Figure 2:
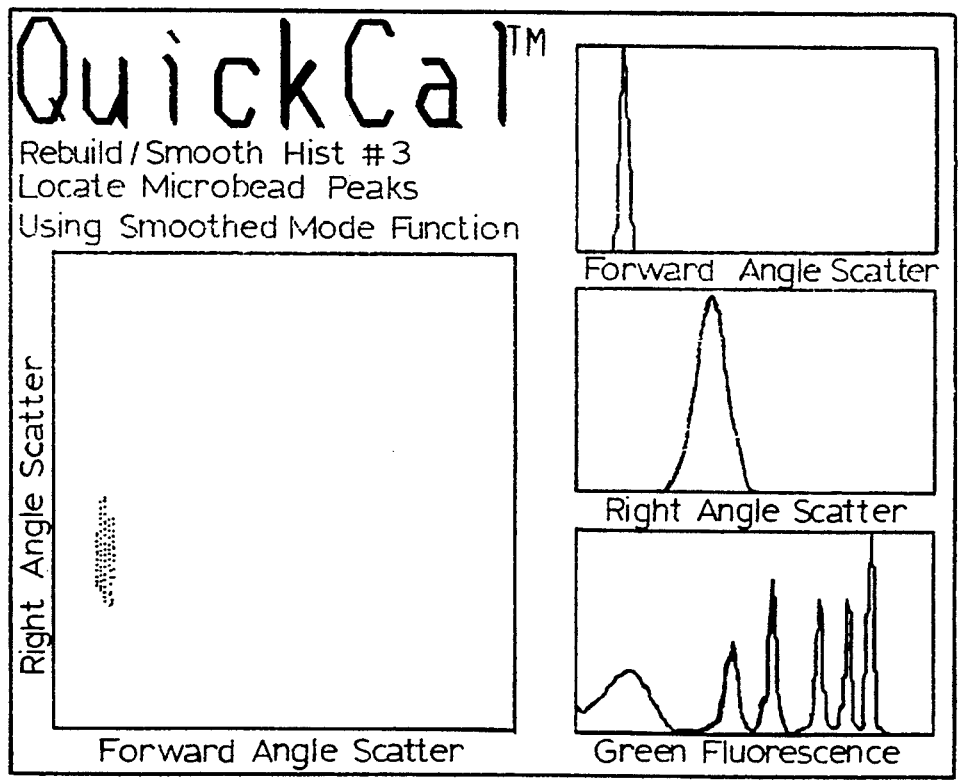
FIG. 2 is a representation of the elements shown in FIG. 1 after smoothing.

A gating routine included in this invention called CleanSweep TM is the second function performed by the first embodiment of the invention. CleanSweep TM sets a numerical threshold on the z-axis and then sweeps away any events which are below this level on the two dimensional histogram (FIG. 2). If more than one population is left after CleanSweep TM is performed (e.g., a large population of doublets) the program saves only the largest numerical population and uses it as a gate. The number of events in the gate is indicated in the message line. The single histograms are next mathematically smoothed with a center-weighted moving mean, and redrawn from events left in the single gated population of the two dimensional histogram. The process may be followed in the message lines which appear on the screen below the QuickCal TM title header.

Figure 3:
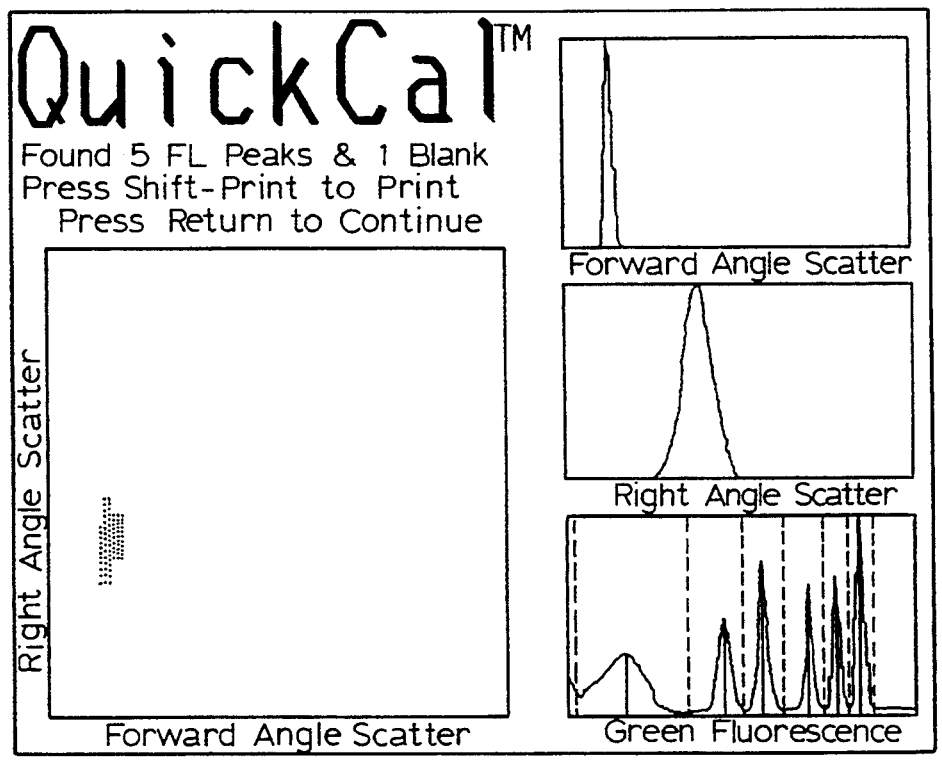
FIG. 3 is a representation of the elements shown in FIG. 2 showing location of peak positions.

The next automatic process is location of the position for markers between the six populations in the green fluorescence channel and determination of the location of the peak of each of these populations. From the smoothed histogram, the program determines peak boundaries and a peak channel number is displayed. This process may take about 15–30 seconds. The message lines under the QuickCal TM header indicate that the program has found five fluorescent peaks and one non-fluorescent peak (FIG. 3). As indicated in the message lines, a copy of the screen can be printed (e.g., by simultaneously holding down the shift and print keys if the computer has a screen dump utility, or an appropriate arbitrary key). Printing the histogram screen may be skipped by just pressing the return key.

Figure 4:
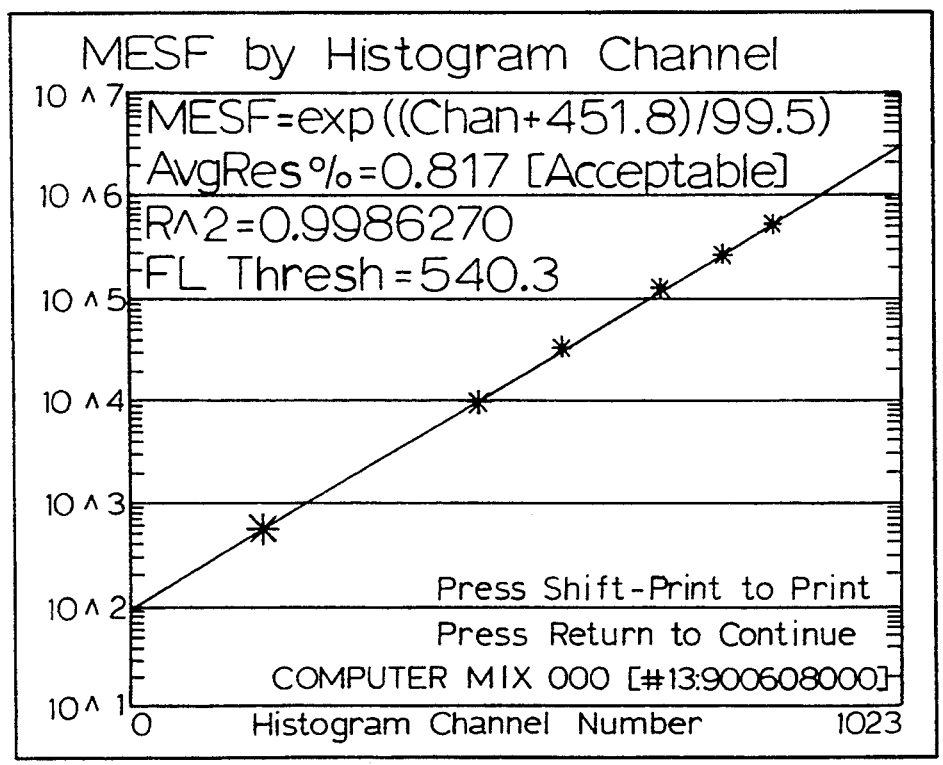
FIG. 4 is a representation of a screen display of the regression line MESF by histogram channel using software of the invention.

The program of the first embodiment next performs a standard linear regression with the assigned MESF values of each of the five standard microbead populations as the independent variables, and the corresponding peak channel numbers as the dependent variables. On the computer screen, the positions of each of the microbead populations is plotted with a small asterisk and that of the blank beads is shown as a large asterisk (FIG. 4). The equation of the regression line is shown on the screen. For each standard, the program compares the MESF value, obtained by a best-fit curve, to the assigned MESF value. The difference between these two values is expressed as a percentage of the assigned standard value and termed the "percent residual difference (Res %)". This percent shows how closely the best-fit curve agrees with the assigned value for each point on the curve. A negative Res % means that the best-fit value is below the assigned value and a positive Res % value is above the assigned value. The program also calculates and displays the Coefficient of Determination ($r^2$) and the average Res % (Av Res %) of the five populations. The Average Residual Percent is the average of absolute residuals expressed as the percent difference from the regression line:

$$\text{AvgRes \%} = 100 * [\text{Absolute(Regression Value} - \text{Actual Value)/Regression Value}]/5$$

Perfect agreement would be indicated by a Coefficient of Determination equal to 1.000 and an Average Residual Percent of 0.000.

The program also displays the goodness of fit. The ranges of each word are as follows:

| Word | Range |
| --- | --- |
| Excellent | 0.000–0.099 |
| Good | 0.100–0.199 |
| Acceptable | 0.200–0.999 |
| Marginal | 1.000–1.999 |
| Unacceptable | >2.000 |

The ranges and their respective words reflect what may be considered a conservative estimate of linearity. These values may be varied if additional information is known about the system, if the accuracy of the results is not essential or if a particular analysis system has different requirements.

The "fluorescence threshold" is considered to be the MESF value of the blank microbeads (if such values can be located on the smoothed histogram), and is the fluorescence noise level below which a true fluorescence signal can not be discerned and MESF values for any analyte are not reliable. The value for fluorescence threshold is related to the sensitivity of the instrument, but it is not a direct measure of sensitivity and may not fully indicate the limitations of the measurement system. For instance, the MESF values for cellular autofluorescence are usually much greater than the fluorescence threshold and may be the limiting factor in sensitivity.

The fluorescence threshold may vary depending on instrument conditions and settlings such as amplifier gain and photomultiplier (PMT) voltage. In general, the fluorescence threshold will be lowest (optimal) when the gains or PMT voltages are high enough to remove the blank microbead population from the zero histogram channel. Under these conditions, unstained cells will usually appear as a distinct peak due to autofluorescence. Increasing the gain or PMT voltage above the lowest settings that give an optimal fluorescence threshold generally does not necessarily improve sensitivity.

The calibration screen can be printed by simultaneously pressing the shift and print keys or an appropriate key combination if the computer's system has a screen dump utility. Pressing the return key initiates printing of a summary report and detailed statistics (FIG. 5). Pressing the stop key at this point terminates the program and keeps the analysis from being placed in the history file which is the next automatic process. For example, in the DOS version, the first time it is run, the program creates a history file in the QUICKCAL directory. Thereafter, each time the QuickCal TM program is run in the DOS version, the analysis of that run is automatically placed in that history file. There is no limit (except for the memory capacity of the computer) to the number of records the history file can hold. Printing and plotting the history file is optional. Selected tabulated data in the history file can be printed by executing a utility program designated as PRH in the DOS version (for example FIG. 6).

Figure 7:
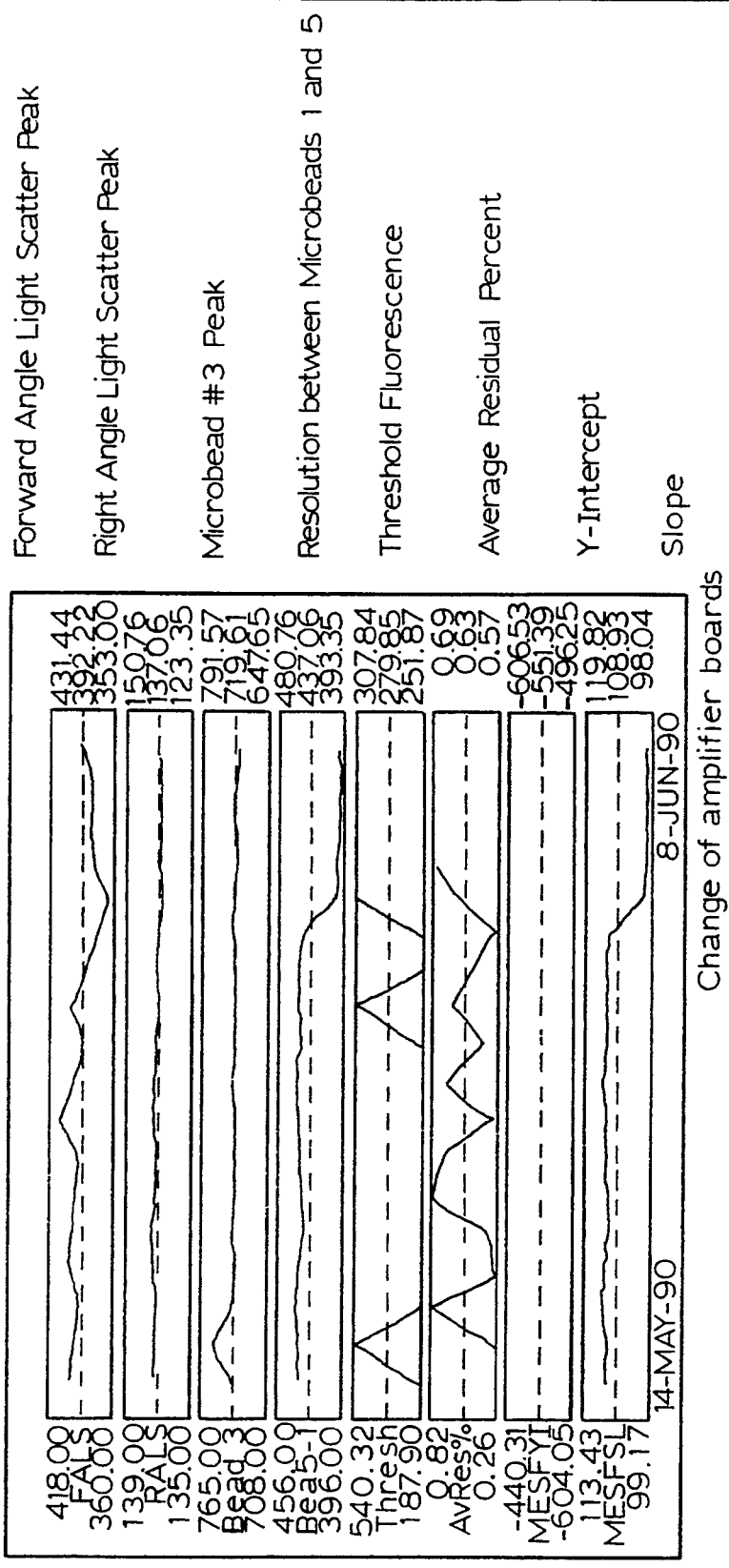
FIG. 7 is a representation of an example of plots of instrument performance for eight parameters using the first embodiment of the invention.

By executing another utility PLH, various parameters in the history file can be plotted as a function of time in a modified Levy-Jennings fashion (FIG. 7). The example default parameters which are plotted (in 2 groups of 3, and 1 group of 2) by pressing the return key are:

Peak channels of the Forward Angle Scatter (Range ±10%)

Peak channel of the Right Angle Scatter (Range ±10%)

Peak channel of the #3 fluorescent population (Range ±10%)

Resolution (difference) between the peak channels of #1 and #5 populations (Range ±10%)

Fluorescence threshold (Range ±10%)

Average Residual Percent (Range ±10%)

Y-intercept of the Regression Line (Range ±10%)

Slope of the Regression Line (Range ±10%)

The range of the fluorescence threshold and average residual percent can be set as desired.

The user has the option of plotting any of the parameters listed in the menu in any combination (limited to 8 at a time in the preferred embodiment). FIG. 7 shows from top to bottom, forward angle light scatter peak, right angle light scatter peak, microbead population no. 3 peak, resolution between microbead populations 1 and 5, threshold fluorescence, average residual percent, Y-intercept and slope. The perturbation on resolution and slope was due to a change in amplifier boards on the flow cytometer. The numerical values printed on the left side of each parameter plot indicate the maximum and minimum values for that parameter in the history file. The numerical values on the right side of each parameter indicate the parameter's mean value with the acceptable range of variation for each parameter. The capability of printing out the history file is particularly valuable in clinical settings.

Monitoring the parameters in the history file parameters serves as a comprehensive indicator of how the instrument has been performing over time.

In the history file, stability of the peak channels of the forward, right angle and green fluorescence (#3 microbead population) indicates reproducible instrument setup, and thus, data comparability over time. Stability of the resolution between populations #1-5, combined with the slope, intercept and Average Residual Percent indicates reproducible response of the instrument over the intensity range, with significant variation in these values possibly indicating instability in the amplifiers. Fluorescence Threshold indicates the fluorescence noise level of the instrument.

In summary, when software of the invention is used with the computer for which it is programmed (e.g. a Hewlett Packard or an Elite TM workstation), the following types of information may be obtained:

(1) a screen showing: a plot of forward angle scatter vs. right angle scatter; a forward angle scatter histogram; a green fluorescence histogram;

(2) same as (1) above out using a smoothed mode function on each portion of the screen;

(3) same as (2) above but the green fluorescence is shown as a vertical dotted lines at the fluorescent peaks; and (4) a plot of histogram channel number vs. MESF, including the equation for the line on the plot, the percentage average residual and whether such percentage is acceptable, the correlation coefficient of MESF and channel no., and the fluorescence threshold.

The software of the first embodiment of the invention may provide the capability of evaluating two or more fluorescence channels at the same time. The kit of the invention then includes two or more separate premixed suspensions of quantitative microbead standards, with each suspension preferably containing five populations of fluorescently labeled microbeads and a blank microbead population. Within each suspension, all labeled microbeads are labeled with the same fluorescent dye with a different dye used for each suspension. For example, the kit may contain one suspension of multiple populations of green-fluorescing microbeads labeled with the fluorescent dye fluorescein; a second suspension of multiple populations of orange-fluorescing microbeads labeled with the fluorescent dye phycoerythrin; and a third suspension of multiple populations of red-fluorescing microbeads labeled with the fluorescent dye PerCP (Becton Dickinson, San Jose, Calif.). Within each suspension all microbeads are highly uniform in size, having a coefficient of variation of diameter of about 2% or less within the suspension, but it is not necessary that the microbeads in each suspension be the same size as those in the other suspensions. The uniformly sized microbeads in each suspension are comprised of a plurality of microbead populations as in the suspension of the first embodiment, with each population having a different fluorescent intensity of the dye used in that suspension. Preferably there are five fluorescently labeled modulations in each suspension plus a blank microbead population.

As when there is only one microbead suspension, a list mode calibration file is obtained. Because of the different fluorescent labels of the suspensions, each is monitored on a different channel. For example, with the three dyes mentioned above, the FL1 channel may have the filters set to monitor fluorescein, the FL2 channel would monitor phycoerythrin, and the FL3 channel would monitor PerCP. The separate tubes containing the three suspensions is run in sequence after being identified by a number on the flow cytometer. The list mode data are automatically collected for each fluorescent dye using the same instrument settings.

The software program is accessed after the list mode data are obtained. The operator indicates which files are desired with the three dyes discussed above, the operator indicates that the FL1, FL2 and FL3 channels are being used. For fewer dyes, fewer channels are designated. The software program provides a histogram of the fluorescence and a dot plot of the first channel, performs the CleanSweep TM function and finds and shows the peaks for the first suspension of microbeads. It then goes to the second channel and does the same analysis, adds the new information to the dot plot, and performs the remaining functions for the second suspension. The third suspension and further suspensions;, if applicable, are run in sequence until completed.

When all list mode data files have been analyzed, the operator simply presses the return key on the computer, and the calibration plots of the fluorescence intensity of each population are displayed on the screen on the same X-Y axis. Because information about more populations is being simultaneously displayed on the screen, the regression analysis equation is preferably not displayed but is provided along with the plots in a written report that is printed when the operator again presses the return key.

All of the data and calculated information for each suspension are placed in a history file. The operator then may plot the same parameters in a modified Levy-Jennings fashion as are possible with the first embodiment. Such plots show in FIG. 8.

The first embodiment of the software of the invention allows the flow cytometer to be monitored for stability and should be run on a daily basis to ensure instrument reliability.

Figure 9:
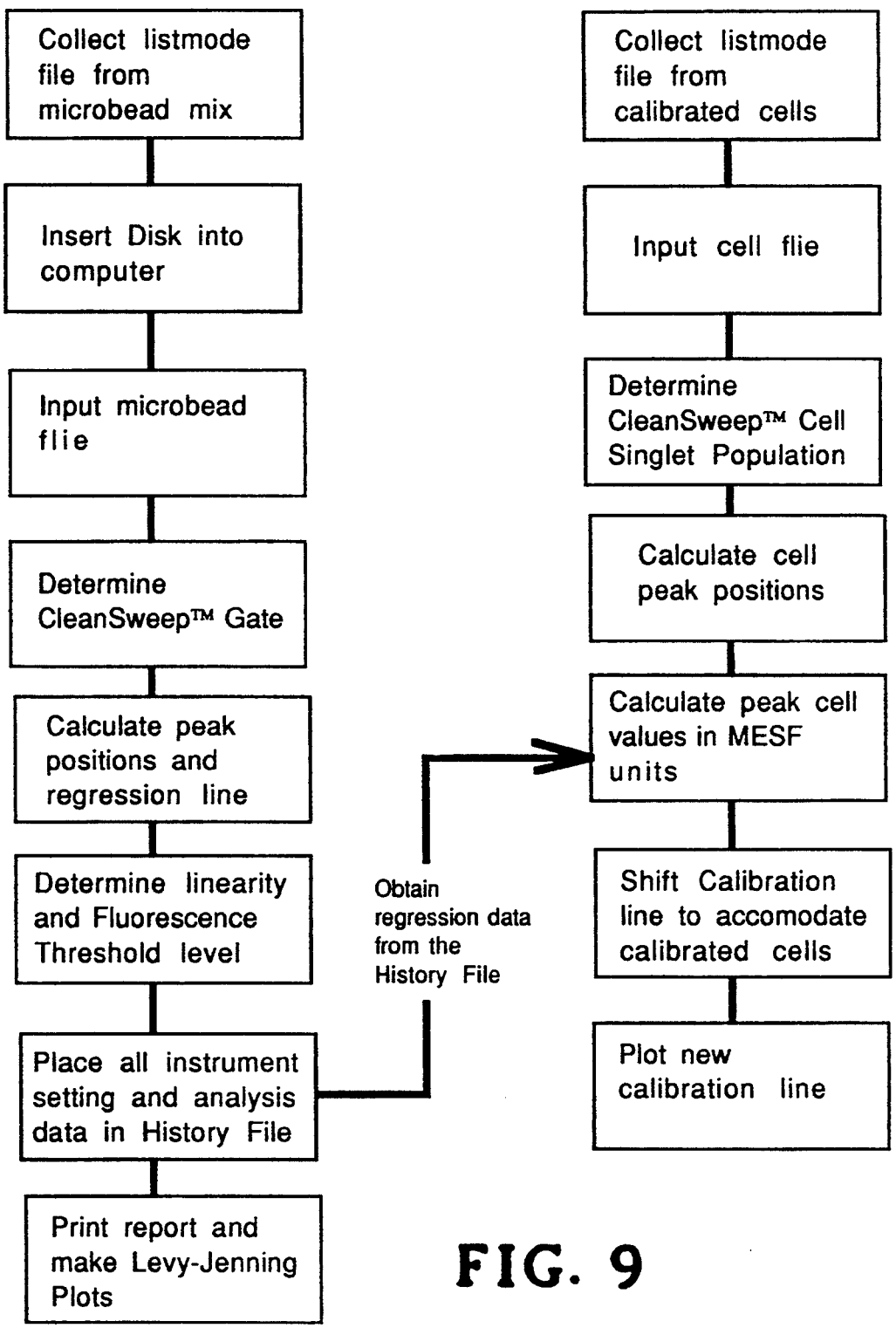
FIG. 9 is a flow chart of the second embodiment of the invention.

In the second embodiment of the invention (FIG. 9), the suspension of labeled microbeads is highly uniform in size, and may also contain calibrated, labeled cells. This software has incorporated within it the data on the known fluorescence of each population of cells. Again, dot plots, CleanSweep TM, and channel fluorescence intensities are shown. The program compares the calibration data for the microbeads and cells and automatically shifts the calibration plot line as defined by the microbeads to coincide with the cell data. A nonautomated procedure for such calibration correction is found in U.S. patent application Ser. No. 07/516,056, filed Apr. 27, 1990.

Figure 10:
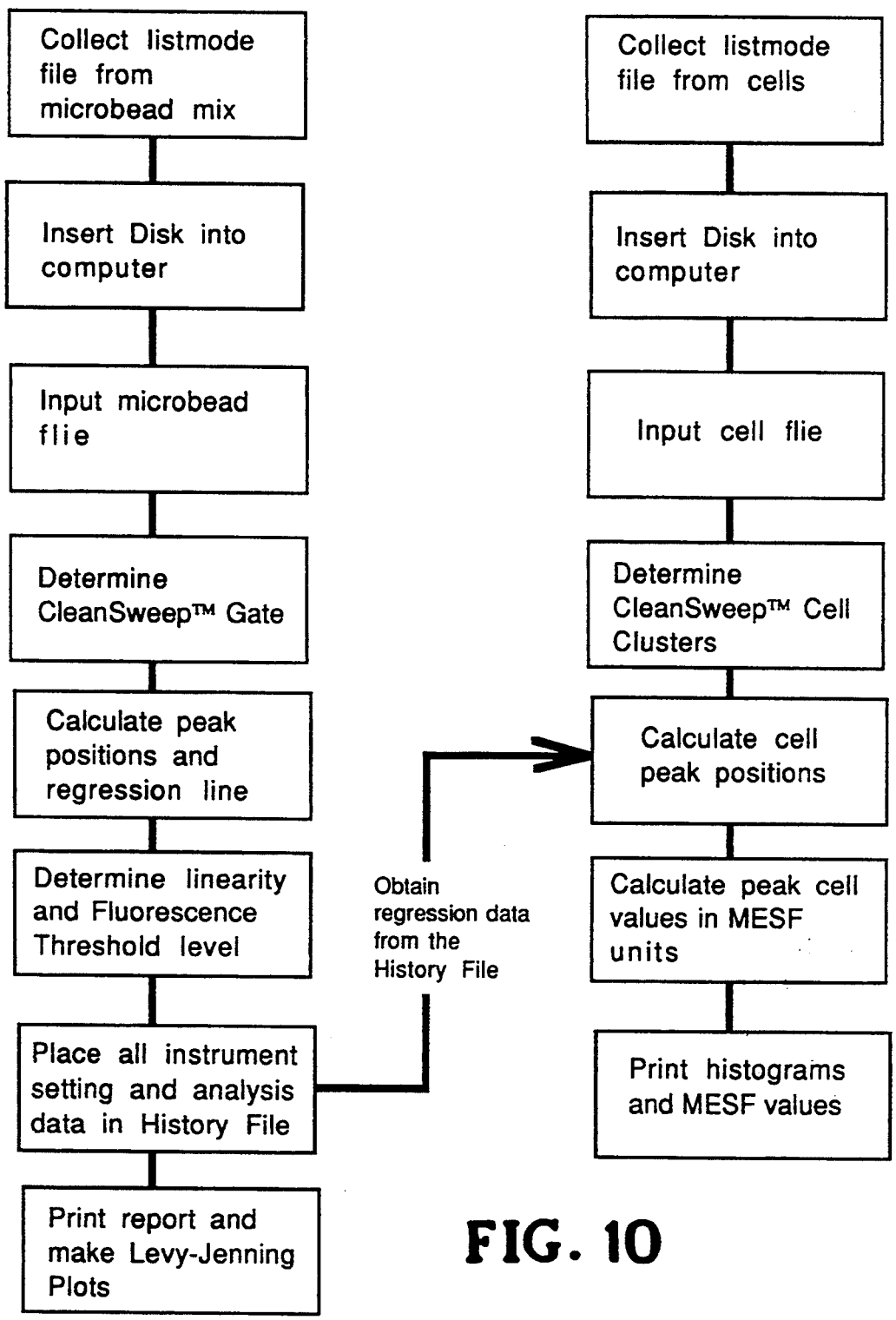
FIG. 10 is a flow chart of the third embodiment of the invention.

In a third embodiment (FIG. 10), a software program termed QuickCal Plus TM, may be provided on the same disk as the other programs for analysis of cell data when samples are run. List mode data files are obtained on unstained and on fluorescently stained cells to be sure that the cells are in the proper intensity range. The standard dot plots and histograms are shown on the terminal screen. The CleanSweep TM function is performed so that clusters of particular cells are isolated, for example, lymphocytes and granulocytes, and possibly monocytes, while those cells not in the clusters still show on the screen, but in an altered shade or color, for example, in a grayer hue than the clustered cell. By pressing function keys, the cut forming the clusters may be adjusted, such as by increasing the cut depth between clusters or by spreading out and enlarging individual clusters. The operator, by mouse manipulations or keystrokes, may put a rectangular box (gate) anywhere on the screen, even after the CleanSweep TM function has been performed, thus manually superseding the software's gating procedure. After the regating procedure, the operator may simply click with the computer mouse in a gated area (or use keystrokes) to have the software do FL1, FL2 and FL3 analysis. As with the microbead standards, fluorescence intensities of the cells are then plotted in each channel. For the various populations of cells that appear on the plot, the operator may use the mouse (or key strokes) to place markers on each side of each population in each channel, followed by obtaining a report showing MESF values font the average cell intensity.

If the operator wishes to go back to reanalyze the cell data, the operator may change the gates and/or markers again and print a new report.

For each analysis, the operator may print the screen to obtain hard copy of the histograms, and then print the statistics by activating a box on the screen, all of which information may be then obtained on a single sheet of paper. The plots show MESF units and channel and are obtained by using information on slope and Y-intercept of the linear regression plot.

Figure 11:
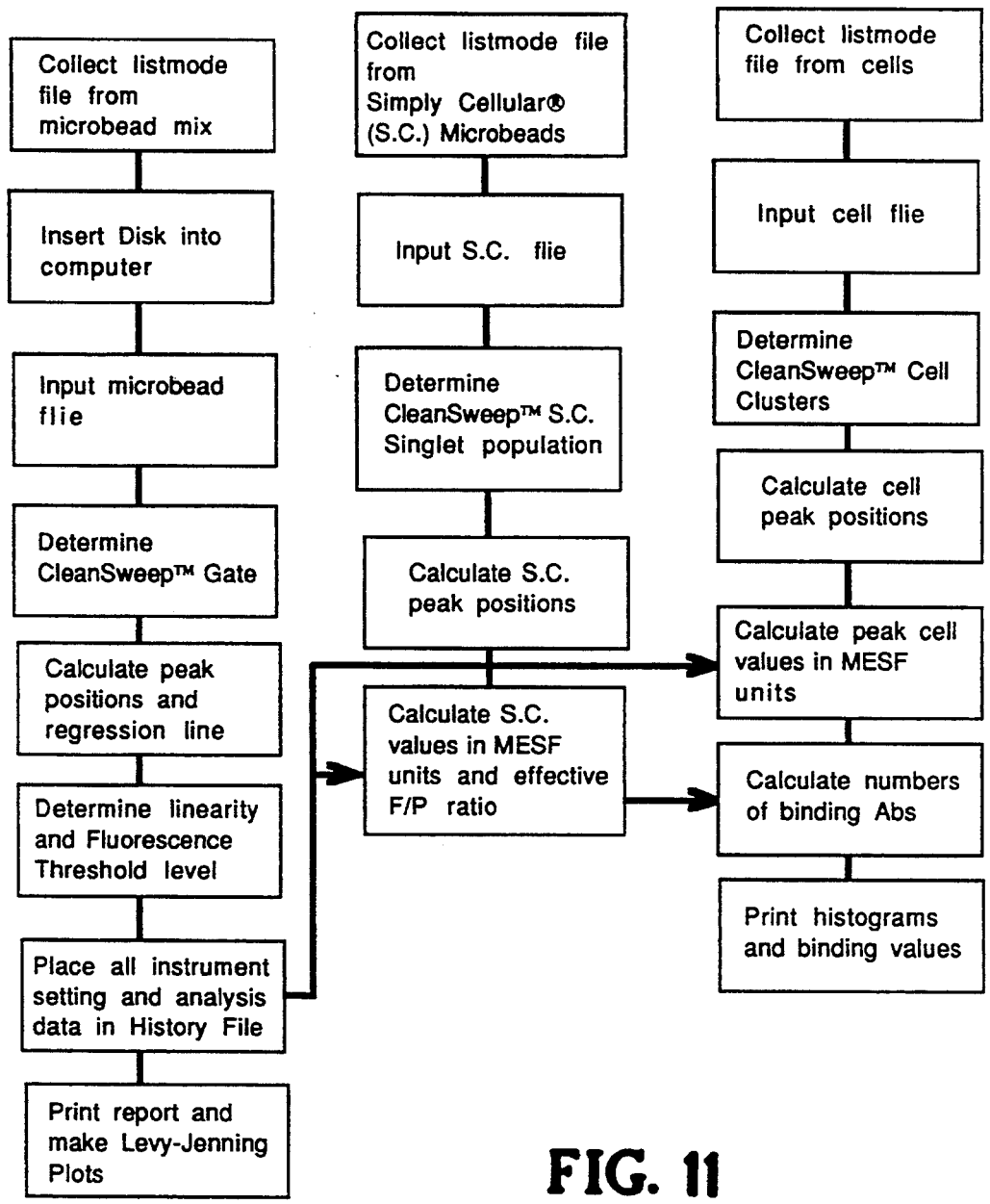
FIG. 11 is a flow chart of the fourth embodiment of the invention.

In a fourth embodiment (FIG. 11), a software program is used by the flow cytometer operator to analyze a mixture of the fluorescent microbeads calibrated to bind a known number of antibodies. The kit of the invention, in addition to the fluorescent microbeads and software discussed above, may also contain microbeads capable of binding a predetermined number of fluorescent antibodies (herein called Simply Cellular ® microbeads). Such microbeads are particularly useful in transplant donor matching, where antibodies against donor tissue are determined prior to doing a transplant.

The program then calculates the effective fluorescence F/P ratio, as described in U.S. Pat. No. 4,918,004, by dividing the fluorescence intensity in terms of equivalent soluble fluorescent molecules by the number of antibody molecules binding to the calibrated microbeads (calibrated with respect to the number of antibodies which will bind to the microbeads; the latter information being provided in the software by the manufacturer). This ratio is placed in a history file.

The fluorescence intensity of the calibrated SIMPLY CELLULAR ® microbeads is determined against the regression calibration time stored in the history file.

The calibrated SIMPLY CELLULAR ® microbeads are thus used by the software to determine the latest F/P ratio, the calibration curve for antibody binding, and to convert fluorescence in MESF units on cells to actual numbers of binding antibodies. Such determinations do not need to be made on a daily basis as do the determinations using the fluorescent intensity standardizing microbeads discussed above in association with the first embodiment of the software.

Figure 8:
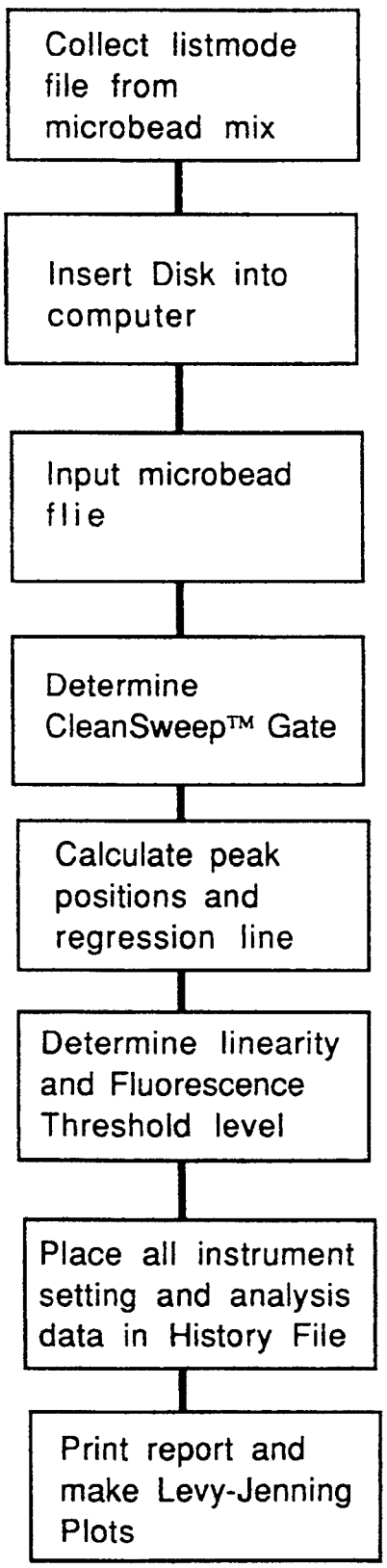
FIG. 8 is a flow chart of the first embodiment of the invention.

The expiration date of the microbeads used in the invention indicates the point in time where the calibrated MESF values of the microbeads have lost fluorescence, and is known from past experience with particular fluorescent dyes and microbeads. The QuickCal TM System is designed to perform for 3–4 months. The expiration date is indicated in the results report, for example, in the upper right hand corner (FIG. 8). Preferably, there are enough microbeads provided in the system (using 100,000 microbeads per run) to perform 100 analyses. This should be enough to do quality control checks on the instrument performance once a day for about three months. After approximately 4 months from the date of an order or about 3 months after receipt of an order, the program stops working. Two weeks before the expiration date, the software indicates that it is time to re-order the QuickCal ™ System.

The software programs of the invention may contain a number of messages indicating; that problems have arisen in the analysis. In general, when a problem is encountered it is best not to re-run the software analysis on the same listmode file, but instead to collect a new list mode file of the microbeads to analyze. The following problem messages are examples of messages that may be found:

The message "AvgRes % [UNACCEPTABLE]" occurs when the Average Residual Percent is greater than 2%. The operator is instructed to check the fluorescence histogram to see if all six peaks have been identified. If one of the middle peaks is skipped by the program, the values plotted will not be correlated and regression will not be correct. Collecting a new listmode file and analyzing generally eliminates this problem. The operator also should be sure that the correct lot of premixed microbeads that come with that particular software is being analyzed, by matching the correct lot number found on the printout of the detailed statistics with the control number on the bottle of microbeads). The operator also should check to see if the filters are correct, undamaged and clean.

The message "Searching for Blank Median" generally occurs when not enough of the blank population was showing for the program to identify and mark the peak channel of the blanks. This will result in an UNAVAIL message on the regression plot for the fluorescence threshold. The operator should be sure that all five populations of the left side of the histogram have been found and that the AvgRes % is stated to be acceptable.

The message "F1 Thres=UNAVAIL" indicates that the program did not find the peak of the blank population. The operator should collect and analyze a new listmode file of the microbeads after increasing the PMT so that at least ¾ of the blank population is visible in the green fluorescence histogram.

The message "NOT ENOUGH PEAKS TO CALIBRATE" indicates that the program was unable to locate at least five of the populations in the green fluorescence histogram. The operator should check to see which peak locations were missed. The peaks may be missed if their shapes are wide and the resolution between them is poor. Such peaks may indicate air in the fluidics, pool alignment or other problems with the instrument.

The features and advantages of the invention will best be understood by reference to the following examples, which are not to be construed as limiting the invention.

EXAMPLES

Example 1

The microbeads used in the system of the invention may be fluorescein-labeled with fluorescein such that their spectra match the labeled cell samples and calibrated in MESF units as disclosed in U.S. Pat. Nos. 4,714,682 and 4,767,206 and in parent applications of the instant application.

Example 2

Before establishing target conditions and creating a history file for specific sample types, it is useful to determine the performance of an instrument over the working range of PMT voltage, amplifier gains and laser settings (if adjustable). This is accomplished by varying each parameter (one at a time) over its range and performing an analysis of list mode files (ungated 5000 events) with the software of the invention at each setting, starting with the highest instrument settings that will place the brightest fluorescence microbead population just on scale, taking list mode files each time the parameter setting is decreased. Thus, on a FACScan instrument, one starts with the FL1 PMT at a voltage of 850 where the brightest population is still on scale and takes list mode files every 50 volts as the voltage is decreased stepwise until the blank microbead population is off scale and the dimmest microbead population is still on scale (approximately a PMT of 450). Alternatively, using a Profile II (Coulter, Hialeah, Fla.), one may start with the FL1 PMT at a voltage of about 1400 where the brightest (#5) population is still on scale and take list mode files stepwise every time the PMT 100 volts drops stepwise until the blank microbead population is off scale and the dim (#1) population is still on scale (PMT about 800). Generally, to save time, this information from such early runs is not used to create a history file. The slope, AvgRes % and fluorescence threshold are monitored as a function of instrument setting to establish the optimal working range of a particular instrument.

Figure 12:
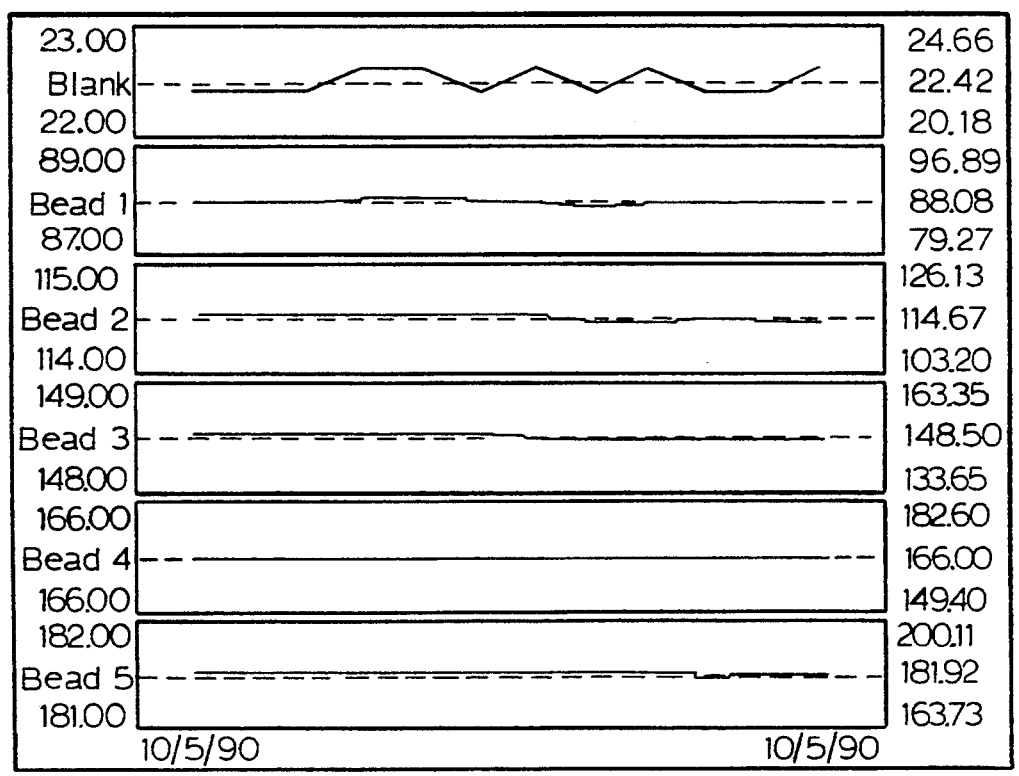
FIG. 12 is a plot of twelve readings on a suspension of microbeads according to the invention.

To determine inherent instrument stability under steady-state conditions once a sample appears acceptably in the light-scatter and fluorescence channels, about 10–12 consecutive list mode files are collected while the standards are aspirating. The list mode files are analyzed with the software and a history file is printed or plotted to show how the eight instrument monitoring parameters vary under steady state conditions, and to establish a base line and determine inherent instrument stability. The change in readings for five fluorescent microbead populations and one blank microbead population within a batch, between 12 readings on one flow cytometer on the same day is shown in FIG. 12 and in Table 1 below. This shows that the fluorescence measurements are stable but the blank is variable related to the threshold fluorescence which is variable due to unstable fluidics.

TABLE 1

| # | AR % | Thresh | MESF-SL | MESF-YI | Peak Channels |
|---|------|--------|---------|---------|---------------|
| 1 | 0.573 | 575 | 23.6 | −127.8 | 22 88 115 149 166 182 |
| 2 | 0.573 | 575 | 23.6 | −127.8 | 22 88 115 149 166 182 |
| 3 | 0.573 | 575 | 23.6 | −127.8 | 22 88 115 149 166 182 |
| 4 | 0.732 | 569 | 23.4 | −125.2 | 23 89 115 149 166 182 |
| 5 | 0.732 | 569 | 23.4 | −125.2 | 23 89 115 149 166 182 |
| 6 | 0.573 | 575 | 23.6 | −127.8 | 22 88 115 149 166 182 |
| 7 | 0.714 | 601 | 23.5 | −127.6 | 23 88 115 148 166 182 |
| 8 | 0.745 | 624 | 23.8 | −131.5 | 22 87 114 148 166 182 |
| 9 | 0.926 | 618 | 23.6 | −128.9 | 23 88 114 148 166 182 |
| 10 | 0.649 | 560 | 23.4 | −125.9 | 22 88 115 148 166 181 |
| 11 | 0.926 | 592 | 23.6 | −128.9 | 22 88 114 148 166 182 |
| 12 | 0.926 | 618 | 23.6 | −128.9 | 23 88 114 148 166 182 |

Example 3

A FACScan ™ flow cytometer (Becton-Dickinson Immunocytometry Systems, San Jose, Calif.) is set up using the first embodiment of the invention to quantitate fluorescence by analyzing list mode files. The flow cytometer is fully aligned and set at the appropriate target conditions, e.g., FL1 PMT 650. A bottle of the pre-mixed microbead suspension of the invention is vigorously shaken, and 2–3 drops of the suspension is diluted in 0.5 ml of any diluent normally used for cell suspensions, e.g. Phosphate Buffered Saline (PBS) at pH 7.2.

Any microbead suspension as described in Example 1 is run on the instrument at a rate of 200–800 events per second. The linear amplifier on forward and side scatter channels, and the log amplifier on the FL1 (green) and FL2 (red) channels are used, and these parameters are set up in the order monitored so that the list mode data is in order and the software program can read the file.

To obtain a fluorescence threshold value, the operator of the machine makes sure that at least about $\frac{3}{4}$ of the blank bead population (the peak on the left of the graph) is visible. Using the acquisition program which comes with the flow cytometer, for example, the C30, FACScan Research Software or Lysys II for Becton Dickinson flow cytometers, an ungated file of 10,000 events is collected.

Example 4

First Embodiment

As in Example 3, the instrument is set up using both the FL1 and FL2 fluorescence channels. A listmode file is obtained from a suspension of the premixed FITC labeled, calibrated microbead standards and then a separate listmode file is obtained from a suspension of the pre-mixed phycoerythrin labeled calibrated microbead standards. The QuickCal TM software program is run, the two listmode files entered, and the program allowed to analyze the data and calculate the regression lines for each channel. QuickCal TM calculated the regression line for the FL1 channel as MESF=exp(Channel+456.2)/92.6 and the regression line for the FL2 channel as MESF=exp(Channel+428.9/112.3.

Example 5

Second Embodiment

The FACScan TM flow cytometer calibrated in Example 3 is used to run an unknown sample of cells labeled with Leu2A-FITC. The fluorescence intensity of cells in MESF units is calculated from the Linear Regression Equation reported in the calibration plot and Summary Report, which is valid because the spectra of the standards match those off the cell samples, and the instrument settings are unchanged when running the cell samples. The intensity determination is accomplished by finding the peak channel of any cell population and using this value in the linear regression equation to calculate the fluorescence intensities of the cells, as follows: MESF of Cells=exp (Peak Channel-Y intercept)/Slope).

For the particular sample of, the peak (mean) of the cell population was in channel 707. The regression equation of the particular instrument was: MESF=Exp ((Channel+451.839)/99.463). Therefore: MESF of Cells=Exp ((707+451.839)/99.463)=Exp (11.6509)=114,800.

Example 6

Second Embodiment

A population of calibrated FITC-labeled calf thymocytes with a calibrated intensity of 58,000 MESF was run on the flow cytometer at the instrument setting of Example 4. The cells were found to fall on the regression line of the FL1 channel at a value of 54,700 MESF. The QuickCal TM software shifted the regression line such that the slope remained 92.6 and the cells fell on the regression line at the value 58,000.

Example 7

Third Embodiment

Using the instrument settings as in Example 4, lysed whole blood labeled with Leu 2a-FITC and Leu 3a-PE were found to have peak channels of 634 and 538, respectively. The cells were analyzed with the QuickCal TM program using the regression equations in Example 4. This yields fluorescence intensities of 129,730 MESF and 27,250 MESF for the Leu 2a-FITC and Leu 3a-PE labeled cells, respectively.

Example 8

Fourth Embodiment

A population of Simply Cellular ® Microbeads calibrated to bind 51,300 IgG mouse monoclonal antibodies (mAbs) were saturated with Leu 2a-FITC. QuickCal TM software analyzed the Simply Cellular ® microbeads in conjunction with the pre-mixed FITC microbeads and the calibrated thymocytes to correct the regression line. The program calculated the effective F/P ratio as 1.8 and a Leu 2a-FITC binding to the cells in Example 7 of 72,072 mAbs.

Example 9

Application for Tissue Typing (Embodiments 1–4)

A donor's cells were suspended in a recipient's serum for an hour at 4° C., washed and labeled with antiHuman IgG-FITC antibody. A population of Simply Cellular ® microbeads conjugated to human IgG and calibrated to bind 37,800 anti-Human antibodies was saturated with anti-Human IgG-FITC antibodies. Listmode files from the cells and microbeads were taken on a flow cytometer whose settings were as in Example 4 and analyzed with the QuickCal TM software. The effective F/P ratio of the antibody was calculated to be 2.3 and the number of antibodies binding to the recipient's cells was 5,800. This value is over the allowable limit of 2,500 binding antibodies and therefore it is most likely that the transplant tissue would be rejected by the recipient.

While the invention has been described with reference to specific embodiments thereof, it will be appreciated that numerous variations, modifications and embodiments are possible, and accordingly, all such variations, modifications, and embodiments are to be regarded as being within the spirit and scope of the invention.

What is claimed is:

1. A kit for automated performance analysis and calibration for a flow cytometer, said kit used with a flow cytometer, a programmable computer and a display screen, said kit comprising:
   (a) a suspension of a plurality of populations of quantitative fluorescent microbeads and a nonfluorescently labeled microbead population in a container, each of said fluorescent microbeads being bound to a first fluorescent dye, said fluorescent microbeads having a useful life, said useful life being designated in said kit; and
   (b) software operating on said computer and containing information on the fluorescence intensity of each population of microbeads, said software operating with said computer to control calculation of calibration and fluorescence information tailored to said microbead populations, and display on said screen an expiration date correlated to the useful life of said microbeads to an operator calibrating said flow cytometer with said microbeads, wherein said software ceases operation on said computer at said expiration date, whereupon said flow cytometer cannot be calibrated with said software and said microbeads and the operator must utilize another suspension of microbead populations and software tailored for use on said computer with said another suspension to calibrate the flow cytometer.

2. A kit according to claim 1, wherein the first fluorescent dye is fluorescein.

3. A kit according to claim 1, further comprising a second premixed suspension of quantitative microbeads, said second suspension comprising a plurality of populations of microbeads, each of said plurality of said populations having microbeads with a uniform size and a distinct fluorescence intensity which differs from the other populations in said second suspension in fluorescence intensity, the microbeads of one of said populations having no added fluorescent dye and the microbeads in the remaining populations being bound to a second fluorescence dye.

4. A kit according to claim 3, wherein the first fluorescent dye is fluorescein and the second fluorescent dye is phycoerythrin.

5. A kit according to claim 3, further comprising a third premixed suspension of quantitative microbeads, said third suspension comprising a plurality of populations of microbeads, each of said plurality of said populations having microbeads with a uniform size and a distinct fluorescence intensity which differs from the other populations in the third suspension in fluorescence intensity, one of said populations having no added fluorescent dye and the remaining populations in said third suspension being bound to a third fluorescence dye.

6. A kit according to claim 1, further comprising a suspension of microbeads capable of binding predetermined numbers of fluorescent antibodies.

7. A kit according to claim 3, further comprising a suspension of microbeads capable of binding predetermined numbers of fluorescent antibodies.

8. A kit according to claim 5, further comprising a suspension of microbeads capable of binding a predetermined number of fluorescent antibodies.

9. A kit according to claim 1, further comprising calibrated, fluorescently labeled cells.

10. A method of calibrating and of determining performance of a flow cytometer, comprising:
(a) providing a flow cytometer, a programmable computer and a display screen;
(b) providing a premixed suspension of quantitative microbeads, said microbeads having a useful life, said microbead suspension comprising a plurality of populations of microbeads, each of said plurality of said populations having microbeads with a uniform size and a distinct fluorescence intensity which differs from the other populations in fluorescence intensity, the microbeads of one of said populations having no added fluorescent dye and the remaining microbeads being bound to a first fluorescent dye;
(c) indicating that the microbeads have a useful life;
(d) providing software operating on said computer and containing information on the fluorescence intensity of each population, said software operating on said computer to control calculation of calibration and fluorescence information tailored to said microbead populations, and display on said screen an expiration date correlated with the useful life of the microbeads to an operator calibrating said flow cytometer with said microbeads, wherein said software ceases operation on said computer at said expiration date, whereupon said flow cytometer cannot be calibrated with said software and said microbeads;
(e) using said flow cytometer and said microbead suspension prior to said expiration date to provide an ungated list mode file of data for the microbead suspension on the flow cytometer; and
(f) using said software and said computer to automatically gate and smooth the data, locate peaks in fluorescence intensity corresponding to each of the microbead populations, construct linear regression plots and determine the fluorescence threshold intensity of the flow cytometer, wherein when said software ceases operation on said computer, said operator must utilize another suspension of microbead populations and software tailored for use on said computer with said another suspension to calibrate said flow cytometer.

11. A method according to claim 10, wherein the first fluorescent dye is fluorescein.

12. A method according to claim 10, further comprising providing a second premixed suspension of quantitative microbeads, said second suspension comprising a plurality of populations of microbeads, each of said plurality of said populations having microbeads with a uniform size and a distinct fluorescence intensity which differs from the other populations in the second suspension in fluorescence intensity, the microbeads of one of said populations having no added fluorescent dye and the microbeads in the remaining populations being bound to a second fluorescence dye.

13. A method according to claim 12 wherein the first fluorescent dye is fluorescein and the second fluorescent dye is phycoerythrin.

14. A method according to claim 12, further comprising providing a third premixed suspension of quantitative microbeads, said third suspension comprising a plurality of populations of microbeads, each of said plurality of said populations having microbeads with a uniform size and a distinct fluorescence intensity which differs from the other populations in the third suspension in fluorescence intensity, the microbeads in one of said populations in said third suspension having no added fluorescent dye and the microbeads in the remaining populations said third suspension being bound to a third fluorescence dye.

15. A method according to claim 10, further comprising providing a suspension of microbeads capable of binding predetermined numbers of fluorescent antibodies.

16. A method according to claim 12, further comprising providing a suspension of microbeads capable of binding predetermined numbers of fluorescent antibodies.

17. A method according to claim 14, further comprising providing a suspension of microbeads capable of binding predetermined numbers fluorescent antibodies.

18. A method according to claim 14, further comprising providing calibrated, fluorescently labeled cells.

19. A kit for automated performance analysis and calibration for a flow cytometer, said kit used with a flow cytometer, a programmable computer and a display screen, said kit comprising:
 (a) a suspension of a plurality of populations of quantitative fluorescent microbeads and a nonfluorescently labeled microbead population in a container, each of said fluorescent microbeads being bound to a first fluorescent dye, said fluorescent microbeads having a useful life, said useful life being designated in said kit; and
 (b) software operating on said computer and containing information on the fluorescence intensity of each population of microbeads, said software operating on said computer to control calculation of calibration and fluorescence information tailored to said microbead populations and display on said screen an expiration date correlated to the useful life of said microbeads to an operator calibrating said flow cytometer with said microbeads, and ceasing operation at said expiration date, wherein said information comprises average residual percent, noise level, and slope and Y-intercept of a regression line of molecules of equivalent soluble fluorescence of the microbead populations versus corresponding peak channel numbers.

* * * * *

UNITED STATES PATENT AND TRADEMARK OFFICE
CERTIFICATE OF CORRECTION

PATENT NO. : 5,380,663
DATED : January 10, 1995
INVENTOR(S) : Abraham Schwartz and Alan D. Hetzel It is certified that error appears in the above-indentified patent and that said Letters Patent is hereby corrected as shown below:

Column 11, line 16, delete ";".

Column 12, line 11, replace "font" with --for--.

(PTO errors)

Signed and Sealed this

Fourteenth Day of March, 1995

Attest:

BRUCE LEHMAN

*Attesting Officer*     *Commissioner of Patents and Trademarks*